United States Patent [19]

Wiltshire

[11] Patent Number: 5,662,130
[45] Date of Patent: Sep. 2, 1997

[54] DENTAL HYGIENE STORAGE APPARATUS

[76] Inventor: Curtis B. Wiltshire, 11 Nomas La., Richmond, Va. 23233

[21] Appl. No.: 512,992

[22] Filed: Aug. 9, 1995

Related U.S. Application Data

[63] Continuation-in-part of Ser. No. 411,503, Mar. 27, 1995, Pat. No. 5,564,446.

[51] Int. Cl.$^6$ .................................................. A45D 40/08
[52] U.S. Cl. ........................ 132/323; 132/309; 132/314; 222/101; 206/369
[58] Field of Search ............................. 206/63.5, 277, 206/362.1, 368, 369; 132/323, 324, 308, 309, 310, 314, 315; 222/92, 93, 101, 214, 386

[56] References Cited

U.S. PATENT DOCUMENTS

| | | |
|---|---|---|
| 368,027 | 8/1887 | Spencer . |
| 1,336,345 | 4/1920 | Cornelius .................................. 132/308 |
| 1,514,018 | 11/1924 | Sharpe ........................................ 222/93 |
| 2,168,080 | 8/1939 | Allen ........................................ 222/101 |
| 2,545,342 | 3/1951 | Choquette ................................ 222/101 |
| 2,812,880 | 11/1957 | Altman .................................... 222/101 |
| 2,837,243 | 6/1958 | Zebnik ..................................... 222/101 |
| 2,936,006 | 5/1960 | Henley ..................................... 222/101 |
| 3,241,721 | 3/1966 | Freemen .................................... 222/93 |
| 4,050,470 | 9/1977 | Miller . |
| 4,121,600 | 10/1978 | Riddick et al. . |
| 4,403,625 | 9/1983 | Sanders et al. . |
| 4,481,962 | 11/1984 | Pesta . |
| 4,638,824 | 1/1987 | De La Hoz . |
| 5,067,503 | 11/1991 | Stile ......................................... 206/63.5 |
| 5,095,924 | 3/1992 | Stanfield . |
| 5,163,561 | 11/1992 | Fitzgerald ................................ 206/369 |
| 5,215,193 | 6/1993 | Dennis . |
| 5,224,501 | 7/1993 | McKenzie . |
| 5,279,315 | 1/1994 | Huang . |
| 5,400,839 | 3/1995 | Cravett .................................... 132/314 |
| 5,564,446 | 10/1996 | Wiltshire ................................. 132/323 |

*Primary Examiner*—Gene Mancene
*Assistant Examiner*—Ralph A. Lewis
*Attorney, Agent, or Firm*—J. Michael Martinez de Andino; McGuire, Woods, Battle & Boothe, L.L.P.

[57] ABSTRACT

A dental hygiene storage apparatus comprising a housing having a removable partition that forms a toothpaste compartment for dispensing toothpaste therefrom. The partition has slots extending along opposite spaced apart side walls with each slot having a removable gear which is connected to a rotating shaft. The shaft is positioned adjacent to and above a compressor plate located within the partition. The shaft is connected to a handle that when turned causes the compressor plate to press against a removable toothpaste container located within the toothpaste compartment. The toothpaste container has a valve extending through the partition's front wall and is adapted to dispense toothpaste. The dental hygiene storage apparatus further includes a top surface with a storage compartment for storing dental floss containers, and several tubular cavities adapted to receive a dental floss device or a toothbrush. The dental hygiene storage apparatus also has a pull out drawer adapted to store toiletries. The dental floss device is comprised of a pair of handles that have spaced apart top and bottom end portions with a gripping section located therebetween. The top end portion of the handles have attachment means for releasably holding a dental floss segment without requiring a user to manipulate with the user's fingers the dental floss segment when attaching the dental floss segment to top end portions of the handles. The dental floss device allows the user to clean a person's teeth without having to manipulate the dental floss segment with the user's fingers.

8 Claims, 10 Drawing Sheets

DENTAL HYGIENE STORAGE APPARATUS

CROSS-REFERENCE

This application is a continuation-in-part of application Ser. No. 08/411,503 now U.S. Pat. No. 5,564,446 for a DENTAL FLOSS DEVICE AND APPLICATOR ASSEMBLY, which was filed on Mar. 27, 1995.

DESCRIPTION

1. Field of the Invention

This invention relates to the field of dental hygiene and, more specifically, to an improved dental hygiene storage apparatus for flossing and brushing the teeth, and for storing dental hygiene equipment for future use.

2. Background Information a. Dental Storage Apparatus

Conventional dental storage apparatuses employed to store, dispense and position various dental hygiene components have included storage devices such as the dental storage apparatus set forth in U.S. Pat. No. 5,215,193 to Dennis wherein a plurality of containers is mounted within a unitary housing having several containers for storing toothpaste, drinking cups, a mouthwash dispenser, a dental floss container and toothbrushes.

U.S. Pat. No. 5,095,924 to Stanfield sets forth a personal toiletry case that has hinged sections for storing toiletry articles within the sections. U.S. Pat. No. 4,481,962 to Pesta sets forth a portable toiletry stand that includes a box portion for containing cosmetic fluid dispensers.

U.S. Pat. No. 4,121,600 to Riddick et al. sets forth an oral hygiene dispenser having a housing with opposite sides having cup dispensers and an interior section forming a fluid compartment to dispense fluid therefrom which includes a spigot, two additional compartments for storing toothpaste and toothbrushes, and a container of mouthwash for filing the fluid compartment.

U.S. Pat. No. 368,027 to Spencer sets forth a toilet case that is compact and which may be used for traveling, that stores a toothbrush, toothpaste or powder, soap and dental floss wound about a card.

These above-mentioned conventional dental storage apparatuses encounter several problems such as not having or storing a dental floss tool that is easy to hold and which allows a user to floss his or her teeth without having to handle the dental floss with one's fingers. Other problems encountered include not having a compartment for storing and dispensing toothpaste through the use of a toothpaste dispenser that has a compressor plate which allows the user to completely empty the toothpaste dispenser prior to replacing the toothpaste dispenser. Further, the above-mentioned apparatuses do not include or store a toothbrush with a shock-absorbing removable toothbrush head.

In order to overcome the above-mentioned defects in a dental storage apparatus, there is a need for an improved dental hygiene storage apparatus that includes a dental floss tool that allows individuals to quickly and easily engage a strand of dental floss without having to manually handle or tie the dental floss strand to the dental floss tool. There is also a need for an improved dental hygiene storage apparatus which provides for enhanced storing and handling of dental hygiene components such as a toothbrush with a removable section that has a shook-absorbing toothbrush head. There is also a need for an improved dental hygiene storage apparatus that has a toothpaste dispenser that has a compressing means and an automatically closing clip capable of returning to an original closed configuration after having been opened for dispensing of toothpaste. Additionally, there is a need for an improved dental hygiene storage apparatus that facilitates the ready access and use by an individual to the toothpaste, toothbrush, and dental flossing tools which would be used on a daily basis.

b. Dental Floss Applicator and Assembly

Further, conventional dental storage apparatuses may have dental floss devices that employ methods to floss the teeth which encounter several problems. One such problem is the inability to easily hold dental floss without getting one's fingers and hands wet, cutting off the blood circulation in the fingers, or being able to reach the teeth far back into the mouth. A variety of dental floss devices have been suggested in the prior art to facilitate the handling of dental floss to remove food particles, plaque, and tartar from teeth. Dental floss is normally held in the hands and moved by the fingers to insert the dental floss in between two adjacent teeth. Prior art devices, such as the Miller U.S. Pat. No. 4,050,470, the Sanders et al. U.S. Pat. No. 4,403,625, the De La Hoz U.S. Pat. No. 4,638,824, the McKenzie U.S. Pat. No. 5,224,501, and the Huang U.S. Pat. No. 5,279,315 have suggested various ways for using dental floss.

The Miller '470 patent discloses a dental floss holder and applicator assembly that uses handles which have a strand of dental floss secured to the handles through the use of a slot that extends the length of the handles. The Sanders '625 patent discloses a disposable buccal hygienic device that can be separated into two separate ends which are connected by a strand of dental floss. The De La Hoz '824 patent discloses a dental floss device that has two separate flat dental floss securing rings that are connected by a strand of dental floss. The McKenzie '501 patent discloses the use of a pair of separate handles connected to a loop of dental floss, which is attached to the handles by either looping and gluing the strands of floss through holes located at the end of each handle, or by tying or stapling the floss strand ends to the handles. The Huang '315 patent discloses a dental floss assembly having a holder portion with a chamber for storing dental floss, a locating member mounted on the holder portion, and a holding member that is mounted on the locating member, with the holding member having a strand of dental floss mounted thereon. The Huang '315 patent device includes the use of a pin to change the angle of the holding member with respect to the locating member.

Prior art devices, which include the above-mentioned, require the user to manually insert or attach the dental floss strand to the respective holder devices to allow the user to floss his or her teeth. Further, the prior art devices require the user to either dispose of the dental floss holder or to press down on the holder to change the angle of a dental floss holding member with respect to a locating member.

In order to overcome the above-mentioned defects for flossing the teeth, there is a need for a dental hygiene storage apparatus that includes a dental floss device and applicator assembly that allows individuals to quickly and easily engage a strand of dental floss without having to manually tie or attach the strand to the device. There is also a need for a dental hygiene storage apparatus that has a dental floss device and applicator assembly which includes two handles, with each handle having a connecting end that is pushed or stabbed against a dental floss strand to anchor and engage the dental floss strand in place allowing the user to insert the dental floss in place for cleaning the spaces between the teeth. Further, there is a need for a dental hygiene storage apparatus that stores a dental floss tool, which includes two handles, with each handle having a connecting end that is pushed or stabbed against a dental floss strand to anchor and engage the dental floss strand in place allowing the user to insert the dental floss in place for cleaning the spaces between the teeth. There is also a need for a dental hygiene storage apparatus that stores containers having dental floss strands.

SUMMARY OF THE PRESENT INVENTION

Accordingly, it is the primary object of the present invention to provide a dental hygiene storage apparatus that includes a dental floss tool that engages a strand of dental floss for cleaning the spaces between the teeth without having to manually wrap the dental floss around their finger, or tie or attach the dental floss to a handle holding device.

It is a further object of this invention to provide a dental hygiene storage apparatus that includes a toothpaste dispenser that stores and dispenses toothpaste and which includes a toothpaste container, a handle connected to rotatable gears having a compressor plate attached thereto, and an automatically closing clip attached to a valve and capable of returning to an original closed configuration after having been opened for dispensing of toothpaste, with the handle when rotated adapted to cause the compressor plate to press against and squeeze the toothpaste container such that when the automatically closing clip is opened the toothpaste is allowed to flow through the valve for use by an individual.

It is another object of this invention to provide a dental hygiene storage apparatus that stores toothbrushes that have a removable piece with a shock-absorbing toothbrush head.

It is another object of this invention to provide a dental hygiene storage apparatus that is able to be made at a low cost of manufacture with regard to the labor and materials, and which can then be commercially sold at reduced prices to provide a dental hygiene storage apparatus that is economically available to the consumer public.

It is a further object of this invention to provide a dental hygiene storage apparatus that includes a dental floss tool, a toothpaste dispenser, and toothbrushes, with the dental floss tool operative to engage a strand of dental floss for cleaning the spaces between the teeth without having to manually wrap the dental floss around their finger, or tie or attach the dental floss to a handle holding device; the toothpaste dispenser operative to store and dispense toothpaste and which includes a toothpaste container, a handle connected to rotatable gears having a compressor plate attached thereto, and an automatically closing clip attached to a valve and capable of returning to an original closed configuration after having been opened for dispensing of toothpaste, with the handle when rotated adapted to cause the compressor plate to press against and squeeze the toothpaste container such that when the automatically closing clip is opened the toothpaste is allowed to flow through the valve for use by an individual; and the toothbrushes having a removable piece with a shock-absorbing toothbrush head.

Other objects and advantages of this invention will become apparent from the following description taken in connection with the accompanying drawings wherein are set forth, by way of illustration and example, certain embodiments of this invention.

DETAILED DESCRIPTION OF THE PREFERRED EMBODIMENTS OF THE INVENTION

Figure 1:
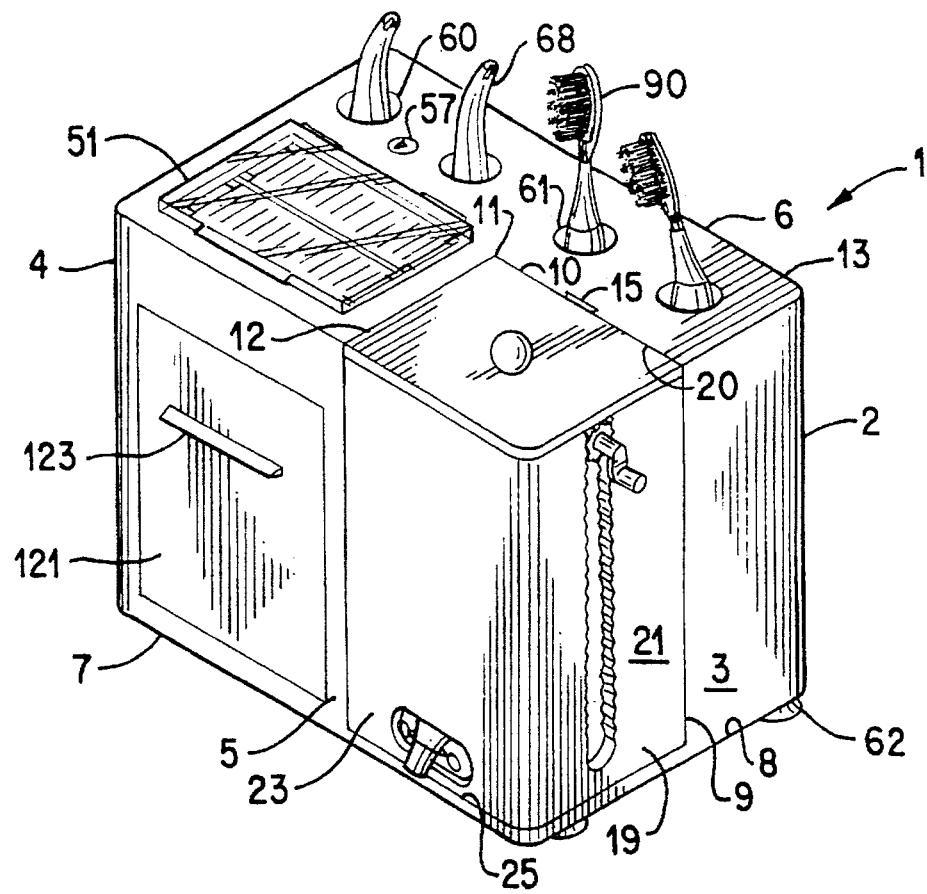
FIG. 1 is a perspective view of a typical embodiment of the dental hygiene storage apparatus showing said storage apparatus having a dental floss tool, toothbrushes, storage compartments for the dental floss strands and a toothpaste dispenser.

Before the present dental hygiene storage apparatus is described, it is to be understood that this invention is not limited to a particular dental hygiene storage apparatus, as such may, of course, vary. It is also to be understood that the terminology used herein is for the purpose of describing particular embodiments only, and is not intended to be limiting as the scope of the present invention will be limited only by the appended claims.

Unless defined otherwise, all technical terms used herein have the same meaning as commonly understood by one of ordinary skill in the art to which this invention belongs. Referring now to the drawings, a typical embodiment of the dental hygiene storage apparatus invention is shown in FIGS. 1–4 and 6, and is generally designated by the reference numeral 1.

The dental hygiene storage apparatus 1 comprises a housing 2 having a rectangular shape and formed by two spaced apart first and second side walls 3 and 4 and a first front wall 5 and a first rear wall 6. The first front wall 5 is spaced from the first rear wall 6 by a floor 7, which extends coextensively from first and second side walls 3 and 4 along a lower continuous edge 8. The first side wall 3 extends from the first rear wall 6 to approximately midway between the spacing between the first front distal end wall 5 and 6, and terminates at a front distal end 9 of side wall 3. Connected to and integral with the front distal end 9 of side wall 3 is an inside back wall 10 that extends along the floor 7 approximately midway between the spacing between the first and second side walls 3 and 4, and which terminates at a corner edge 11. The corner edge 11 is defined by the intersection of the inside back wall 10 and an inside side wall 12. The inside side wall 12 extends from the corner edge 11 along the floor 7 to and is integral with the first front wall 5.

An upper continuous edge 13 is defined by the upper distal ends of the housing first and second side walls and the first front and rear walls 3–6, respectively, and the inside back and side walls 10 and 12, respectively. The upper continuous edge 13 is connected to and integral with a top surface 14 that appears to form an "L" shaped design as seen from FIGS. 2 and 6. The inside back wall 10 has a slot insert 15 that extends along the entire length of the inside back wall 10 from the top surface 14 to the floor 7.

1. Toothpaste Container

Figure 3:
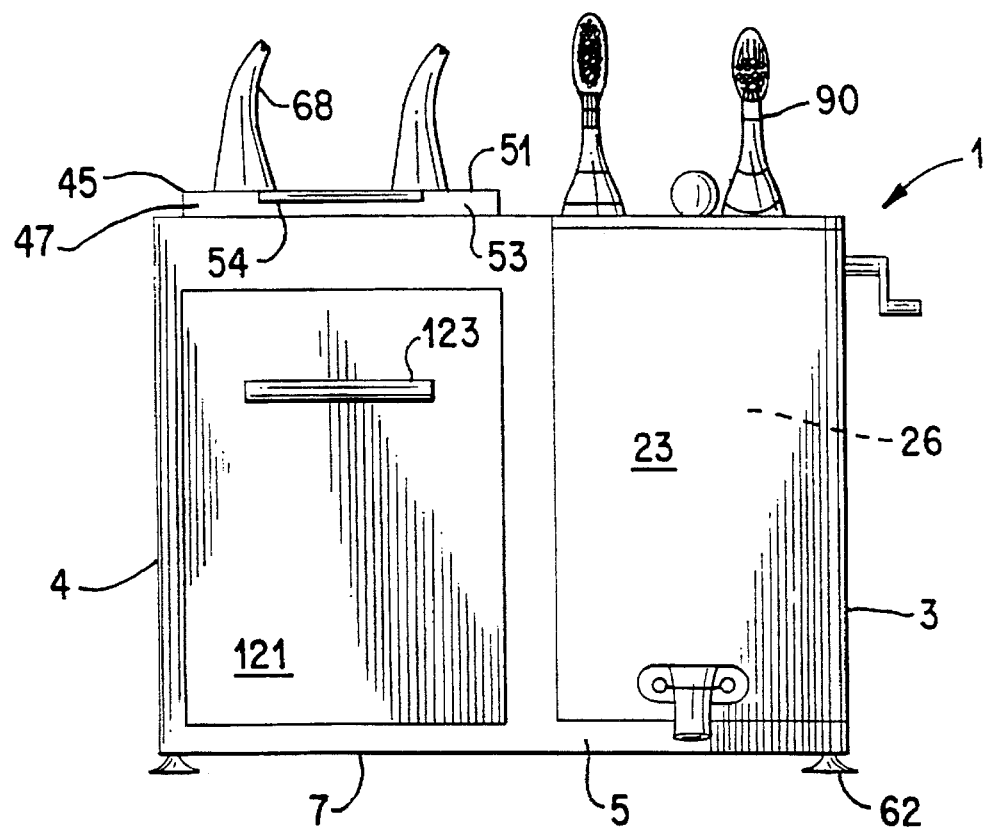
FIG. 3 is a front elevational view of the dental hygiene storage apparatus with the dental floss tool and the toothbrushes stored in said storage apparatus.
Figure 4:
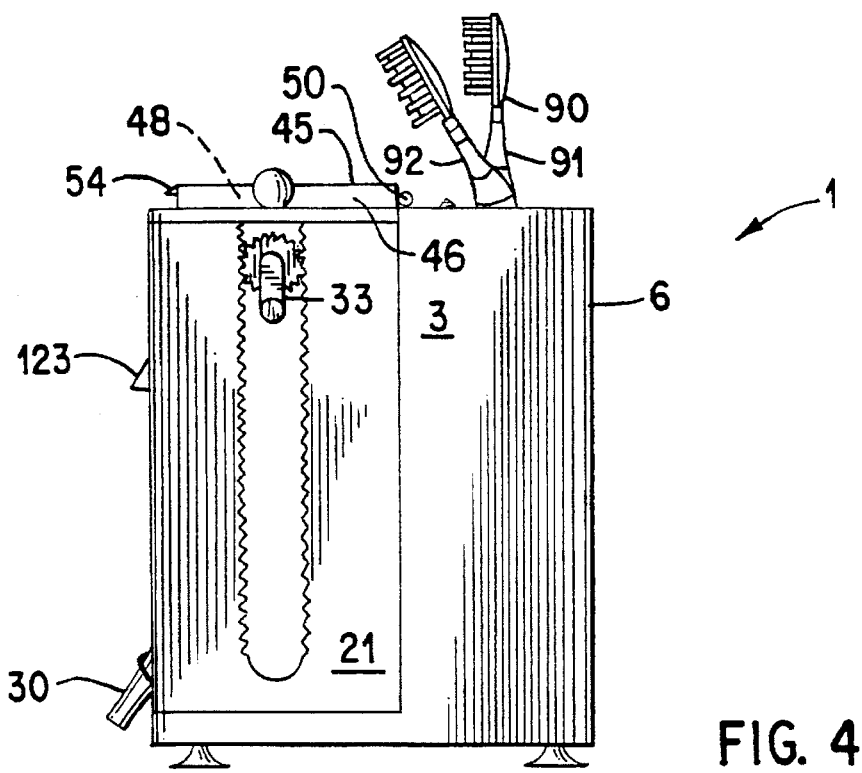
FIG. 4 is a view of the right side of the dental hygiene storage apparatus as viewed from the front of said storage apparatus.
Figure 5:
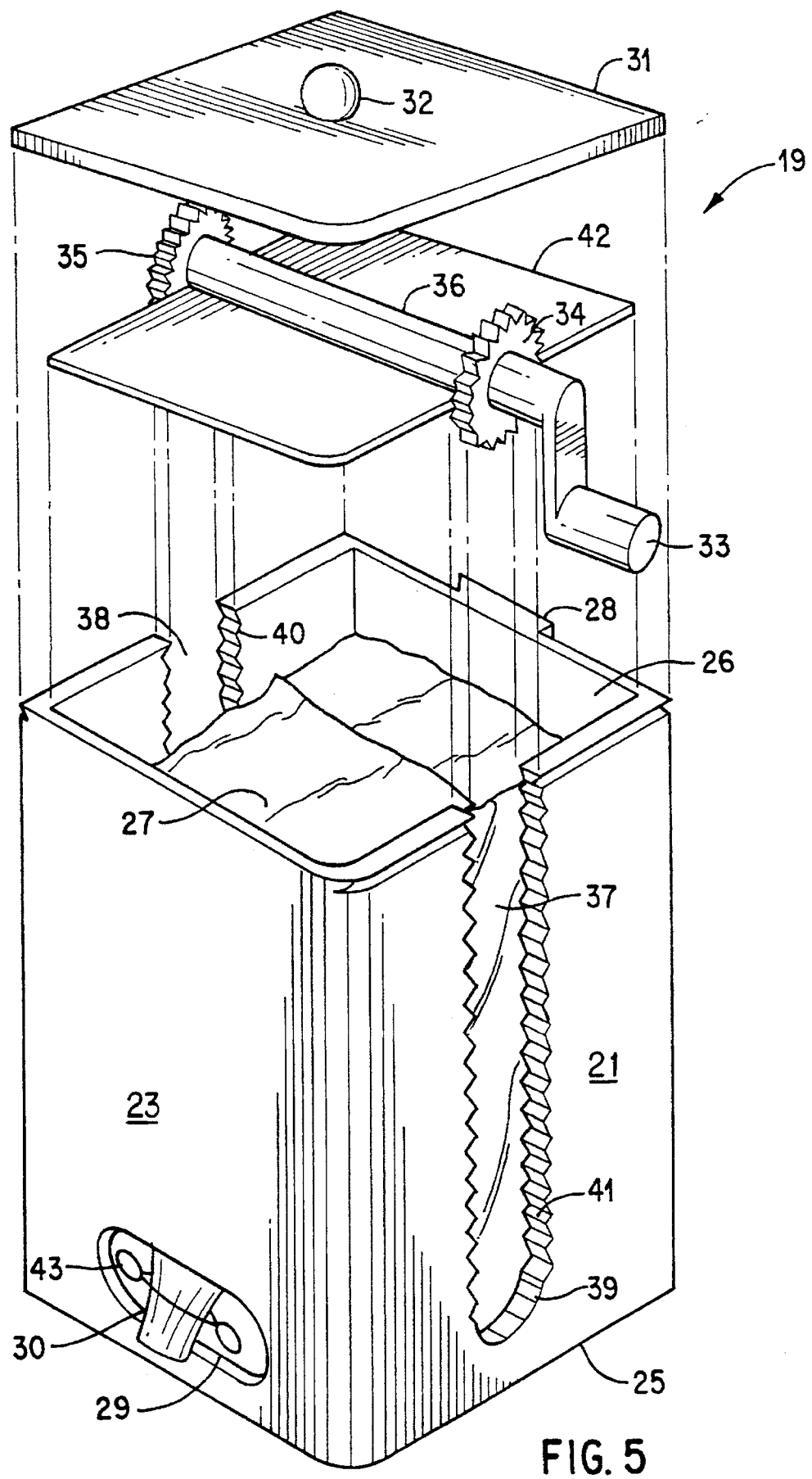
FIG. 5 is an exploded isometric view of the toothpaste dispenser of said storage apparatus.

Referring to FIGS. 1–6, the housing 2 has a first container 19 which has third and fourth side walls 21 and 22, respectively, and second front and rear walls 23 and 24, respectively. The first container 19 extends from an upper end 20 to a bottom 25 to form a first cavity 26. As shown in FIGS. 1 and 5, the first container 19 has a removable and replaceable toothpaste container 27 stored within the first cavity 26. The second rear wall 24 has a slot extension 28 that extends along the entire length of the second rear wall 24. The slot extension 28 is removably insertable into the slot insert 15. The second front wall 23 has an aperture 29 located near the bottom 25 and is approximately midway between the distal opposite edges of the second front wall 23.

The toothpaste container 27 has a toothpaste dispenser valve 30 that extends out from the first cavity 26 through the aperture 29. The toothpaste container 27 can be removably connected to the housing 2 by inserting the slot extension 28 into the slot insert 15. The toothpaste container 27 also has a first lid 31, which has a lid handle 32 mounted thereon. The first lid 31 is removably mounted to the upper end 20 and is able to be oriented relative to and coextensive with upper distal end of the first cavity 26 adjacent to the upper continuous edge 13 of the housing 2. The first lid 31 is adapted to provide when mounted on the upper end 20 a slight inward pressure to the third and fourth side walls 21 and 22, respectively.

Figure 6:
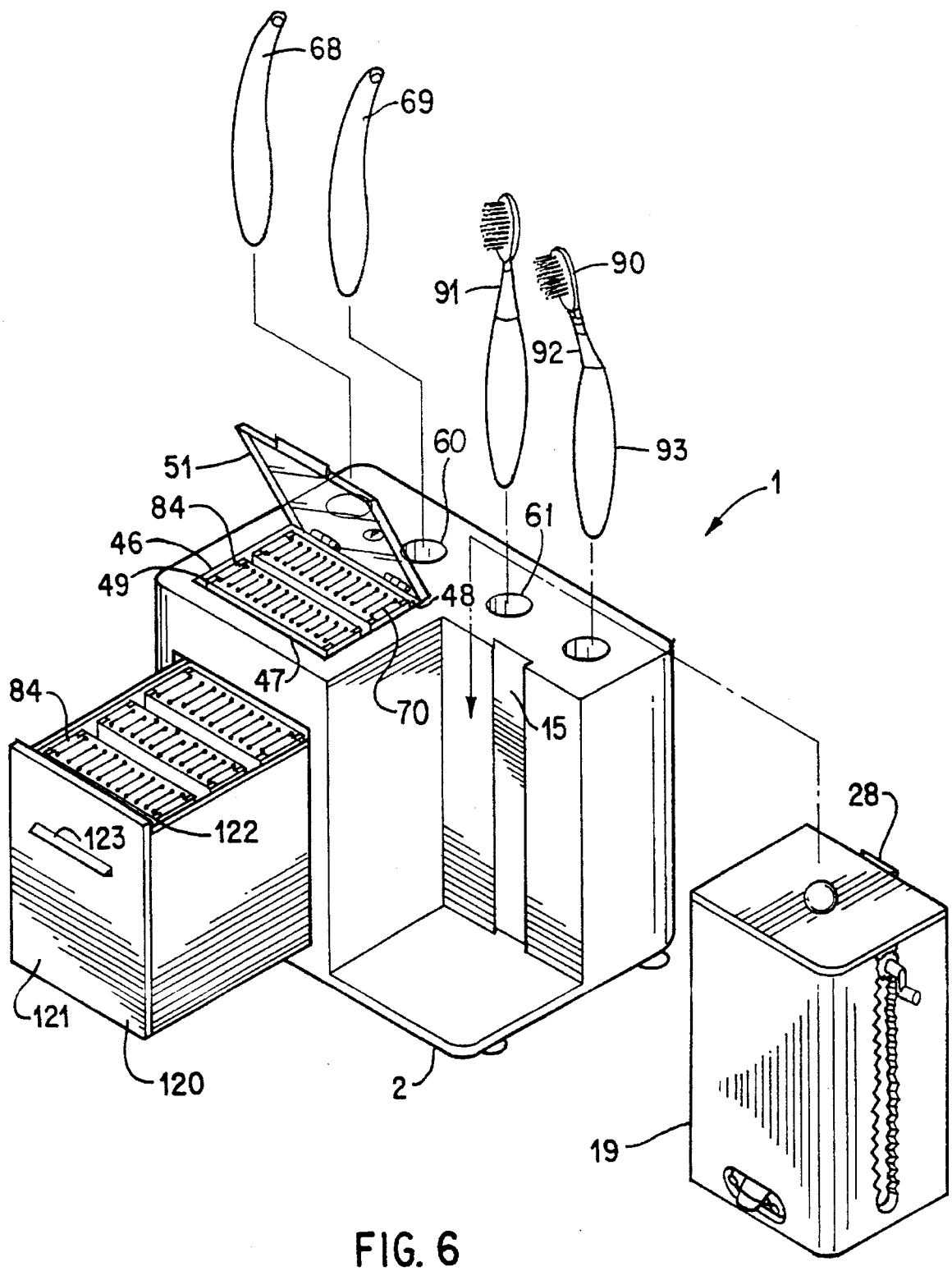
FIG. 6 is an exploded isometric view of said storage apparatus.

As shown in FIGS. 1, 4 and 6, the toothpaste container 27 further has a crank handle 33 that is connected to a first gear 34 and a second gear 35 through a shaft 36. The first and second gears 34 and 35, respectively, travel along first and second slots 37 and 38, respectively, that are located within the third and fourth side walls 21 and 22, respectively. The first and second slots 37 and 38, respectively, extend from the upper end of third and fourth side walls 21 and 22, respectively, to slightly above the bottom 25. The first and second slots 37 and 38, respectively, have first and second slot continuous edges 39 and 40, respectively, which have spaced protrusions 41 extending from the first and second slot continuous edges 39 and 40. The first and second gears 34 and 35, respectively, are adapted to move along the first and second slot continuous edges 39 and 40, respectively, by engaging the spaced protrusions 41.

The handle 33 extends out from the first gear 34 and the third side wall 21. Upon rotatably turning the handle 33 in a counter-clockwise direction, the first and second gears 34 and 35, respectively, travel in a downward direction within the first and second slots 37 and 38, respectively.

The shaft 36 is adapted to be removably positioned above a compressor plate 42 that is placed within the first cavity 26 above the toothpaste container 27. Upon rotation of the shaft 36 by turning the handle 33 in a counter-clockwise direction, the compressor plate 42 is lowered within the first cavity 26 and squeezes the toothpaste container 27. By squeezing the toothpaste container 27 the toothpaste stored within the toothpaste container 27 is more easily dispensed through the toothpaste dispenser valve 30. The toothpaste dispenser valve 30 has an auto-close clip 43 that consists of a resilient engaging wire which is adapted to squeeze and press the toothpaste dispenser valve 30 shut. Upon pressing the ends 44 of the auto-close clip 43 together, the toothpaste dispenser valve 30 is allowed to open thereby allowing toothpaste to flow through the toothpaste dispenser valve 30 after the handle 33 has been turned in a counter-clockwise direction. Upon release of the ends 44 of the auto-close clip 43, the resilient engaging wire of the auto-close clip 43 returns to a "closed" position and once again squeezes and presses the toothpaste dispenser valve 30 shut. Additional turning of the handle 33 in a counter-clockwise direction can cause the toothpaste to flow through the toothpaste dispenser valve 30 even with the auto-close clip 43 in the "closed" position. Upon release of the pressure created by the compression plate 42, the auto-close clip 43 will stop the flow of the toothpaste through the dispenser valve 30.

After the toothpaste within the toothpaste container 27 has been completely used, such that the toothpaste container 27 is empty, the handle 33 can be turned in a clockwise direction which raises the shaft 36 to the top of the first and second slots 37 and 38. The first lid 31 can be removed, which allows the removal of the shaft 36 from the first cavity 26, thereby allowing for the removal of the compressor plate 42 and the empty toothpaste container 27. Additionally, the mere removal of the first lid 31 releases the slight inward pressure to the third and fourth side walls 21 and 22, allowing the shaft 36 to be easily removed or inserted into the first and second slots 37 and 38. Removal of the shaft 36 allows for a new toothpaste container 27 to be inserted within the first cavity 26.

2. Top Storage Area

Referring now to FIGS. 1–6, the housing 2 is shown to have a top storage section that has a second container 45 that has opposite spaced first sides 46 and opposite spaced second sides 47, respectively, and an inside surface 48. The opposite spaced first and second sides 46 and 47, respectively, and the inside surface 48 form a rectangular shaped second cavity 49. Attached to one of the opposite spaced second sides 47 is a pair of hinges 50 that are connected to a second lid 51, which is preferably made of a clear plastic material. The second lid 51 has a handle side 53 which has a protruding lip edge 54 attached hereto. The hinges 50 are attached to the top surface 14 of the housing 2. The protruding lip edge 54 is adapted to allow a user to lift the handle side 53, thereby opening the second container 45 and allowing access to the second cavity 49. Items that can be stored within the second cavity 49 include the rectangular shaped containers 84 which contain dental floss strands 70.

3. Additional Storage Sections and Elements

Figure 2:
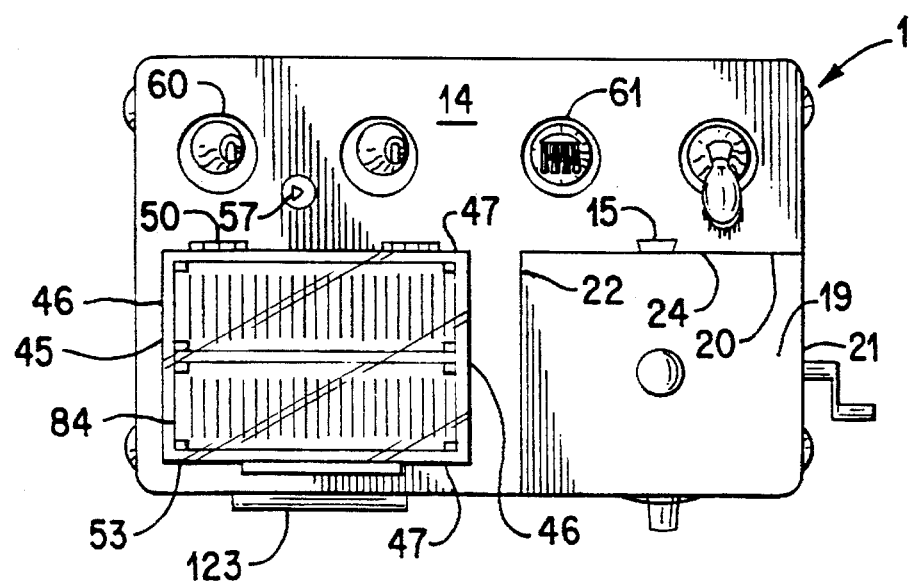
FIG. 2 is a top plan view of the dental hygiene storage apparatus showing the storage compartments for the dental floss tool, the toothbrushes, the storage containers for the dental floss strands, and the toothpaste dispenser.

As shown in FIGS. 1, 2 and 6, the housing 2 has a dental floss strand cutter 57, such as a triangular shaped protrusion that extends from the top surface 14 The housing 2 also has third and fourth cavities 60 and 61, respectively, located near the first rear wall 6 on the top surface 14. The third and fourth cavities 60 and 61 are adapted to store a dental floss tool 68 and toothbrushes 90. As shown in FIGS. 1 and 3, the housing 2 has suction cups 62 located adjacent to each corner of the floor 7. The suction cups 62 are adapted to keep the housing 2 secured to a surface and to prevent the housing 2 from moving when the storage apparatus 1 is in use.

4. Dental Floss Tools

The dental floss tool 68, as shown in FIGS. 1, and 6–9, includes a pair of handle members 69 that are adapted to be connected by a dental floss strand 70, which is approximately one inch in length. The handle members 69 are preferably made of plastic or flexible rubber, but can be made of almost any type of durable material. The handle members 69 have anatomically designed natural grips 72 and are approximately six inches in length. The handle members 69 each have a top end 73 and a bottom end 74, which has an extricator 75 attached thereto. The extricator 75 has a conical shape with a length of approximately ¼ inches.

Figure 7:
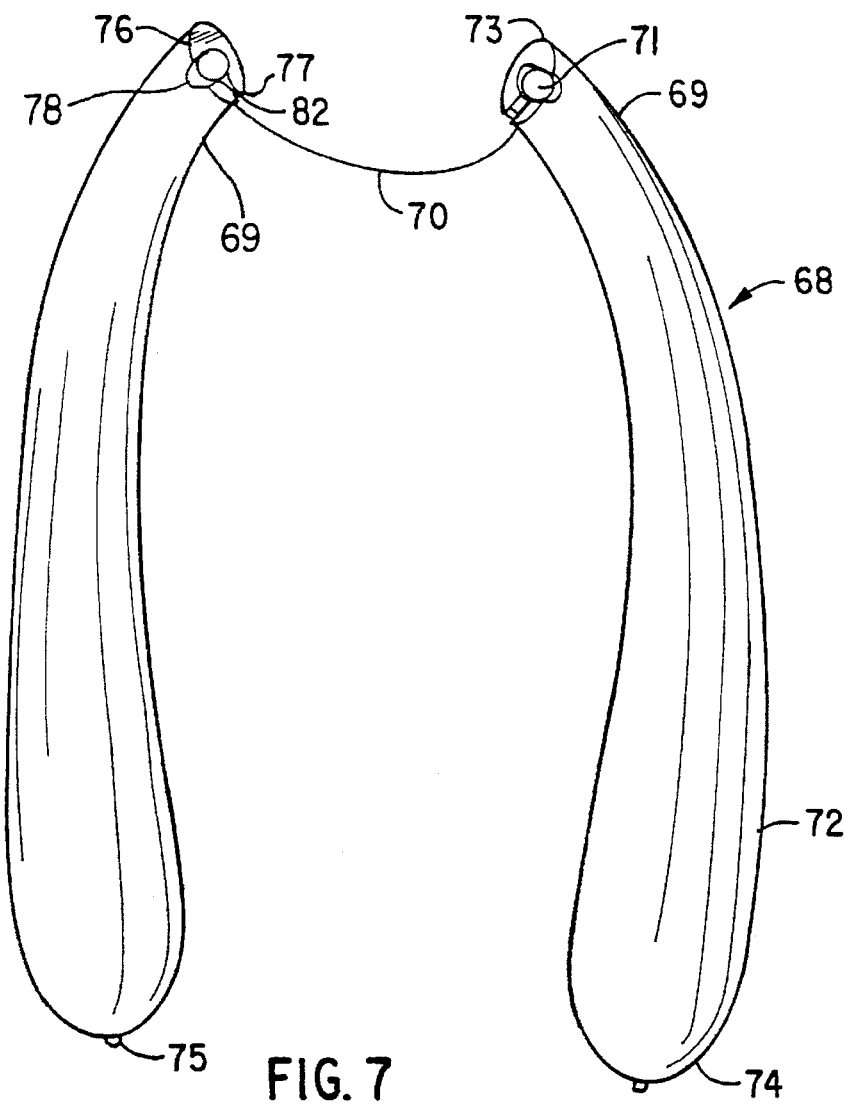
FIG. 7 is a perspective view of the dental floss tool of said storage apparatus with a dental floss strand connecting the two handles of said dental floss tool.
Figure 8:
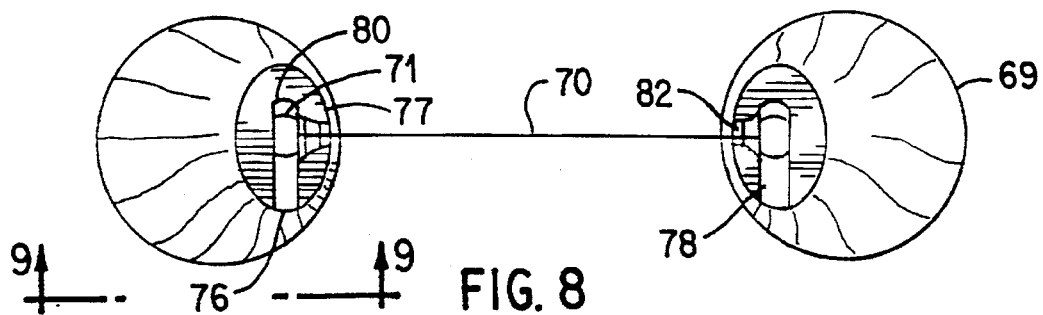
FIG. 8 is a top plan view of the dental floss tool of said storage apparatus with a dental floss strand connecting the two handles of said dental floss tool.
Figure 9:
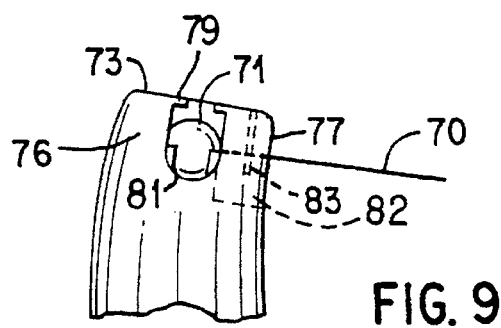
FIG. 9 is a side plan view of the dental floss tool of said storage apparatus taken along lines 9—9 of FIG. 8.

As shown in FIGS. 7–9, the dental floss strand 70 has circular shaped anchors 71 attached to either end of the dental floss strand 70. The anchors 71 are approximately ⅛ inch in diameter and are preferably made of plastic, although any durable and attachable material can be used to make the anchors 71.

Referring to FIGS. 7–9, the top end 73 of the handle members 69 are shown with the dental floss strand 70 connected thereto. The top end 73 has a connecting side 76 and a working side 77. The connecting side 76 has an attachment groove 78 that extends from the surface of the connecting side 76 to midway into the top end 73, and which has a height of approximately ⅜ inches. The attachment groove 78 has placement guards 79 which are located at and extend along the top edges of the attachment groove 78. The attachment groove 78 is designed to easily accommodate the anchors 71 by pushing or stabbing the top end 73 toward one of the anchors 71, which allows the anchor 71 to enter the attachment groove 78. The placement guards 79 prevent the anchors 71 from raising out of the attachment groove 78. The attachment groove 78 has a back end 80 and groove extensions 81, which are located adjacent to the back end 80 and that are attached to and integral with the sides of the attachment groove 78. The groove extensions 81 are designed to allow each of the anchors 71 to slide against the back end 80, but prevent the anchors 71 from sliding back towards the entrance of the attachment groove 78.

The working side 77 of the top end 73 has a slot 82 that extends from the surface of the working side 77 to the attachment groove 78. The slot 82 has a clip 83, which is connected to the top right edge of the slot 82 and extends diagonally into and across the slot 82. The clip 83 is designed to keep the dental floss strand 70 within the slot 82.

As shown in FIGS. 1, 2 and 6, several dental floss strands 70 are stored in rectangular shaped containers 84, which can be placed within the second container 45, in the second cavity 49 under the second lid 51. The rectangular shaped containers 84 can also be placed in a third container 120, such as a pull out drawer 121. The pull out drawer 121 forms a fifth cavity 122 for storing several of the rectangular shaped containers 84.

Figure 10:
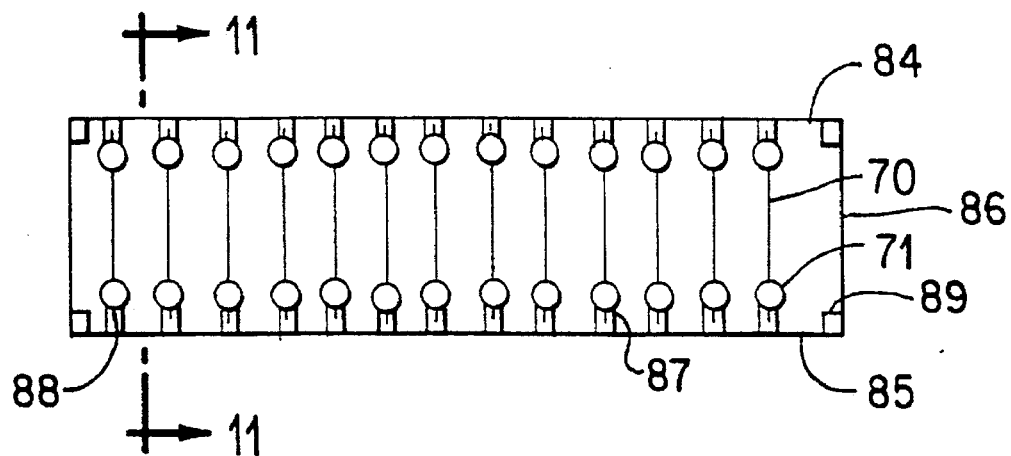
FIG. 10 is a top plan view of a dental floss strand container of said storage apparatus.
Figure 11:
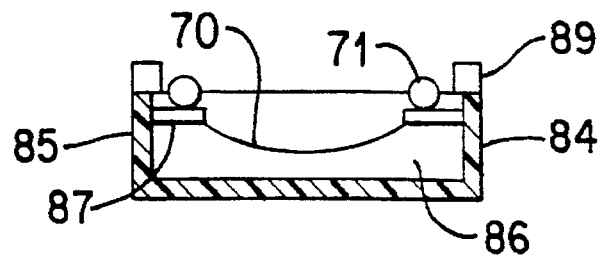
FIG. 11 is an orthographic view of the dental floss strand container taken along lines 11—11 of FIG. 10.
Figure 12:
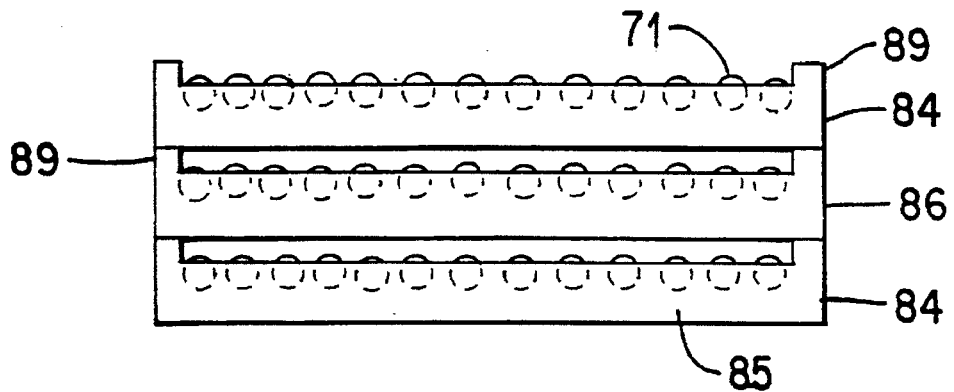
FIG. 12 is a side plan view of several dental floss strand containers mounted on top of each other.

Referring to FIGS. 10–12, the rectangular shaped containers 84 have opposite spaced sides 85 and opposite spaced ends 86. The opposite spaced sides 85 which have support notches 87 that are located on the inner surfaces of the opposite spaced sides 85. The support notches 87 can alternatively be attached to the top edges of the opposite spaced sides 85. The dental floss strand 70 is removably inserted into the thin slots 88 that are formed within the support notches 87, while the anchors 71 lie on the top surface of the support notches 87. The rectangular shaped containers 84 also have stacking bars 89 which extend vertically from the top edges of the corners formed by the intersection of the opposite spaced sides 85 and opposite spaced ends 86. As shown in FIG. 12, through the use of the stacking bars 89, the rectangular shaped containers 84 can be stacked one on top of another and can then stored be within the third container 120 for future use.

An alternate embodiment of the dental floss strand 70 (not shown) can consist of a circular or a looped strand of dental floss, which preferably has an approximate length of one inch.

5. Toothbrushes

Figure 13:
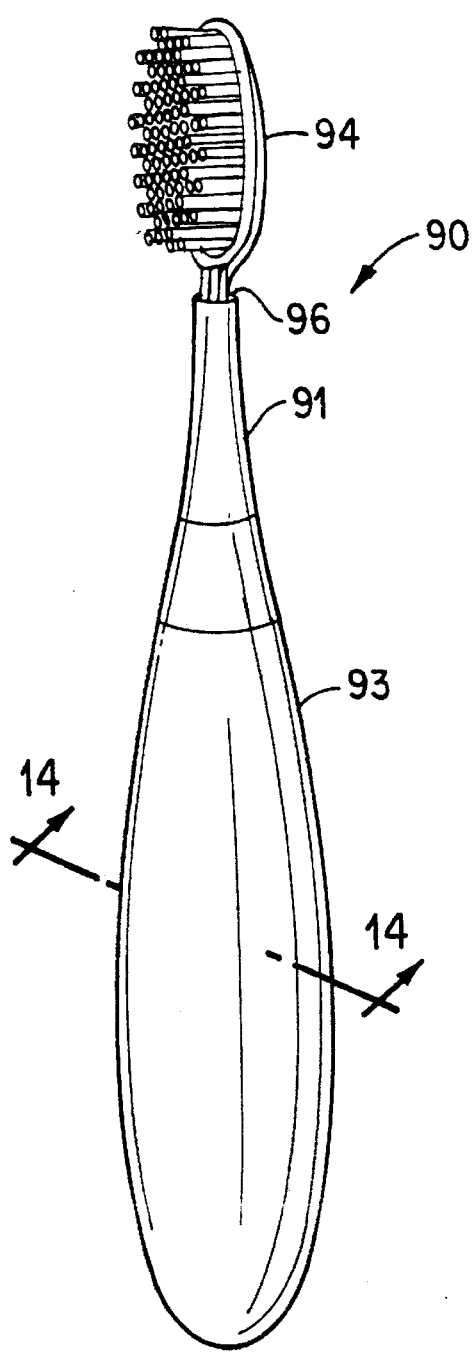
FIG. 13 is a perspective view of a non-slanted toothbrush of said storage apparatus.
Figure 14:
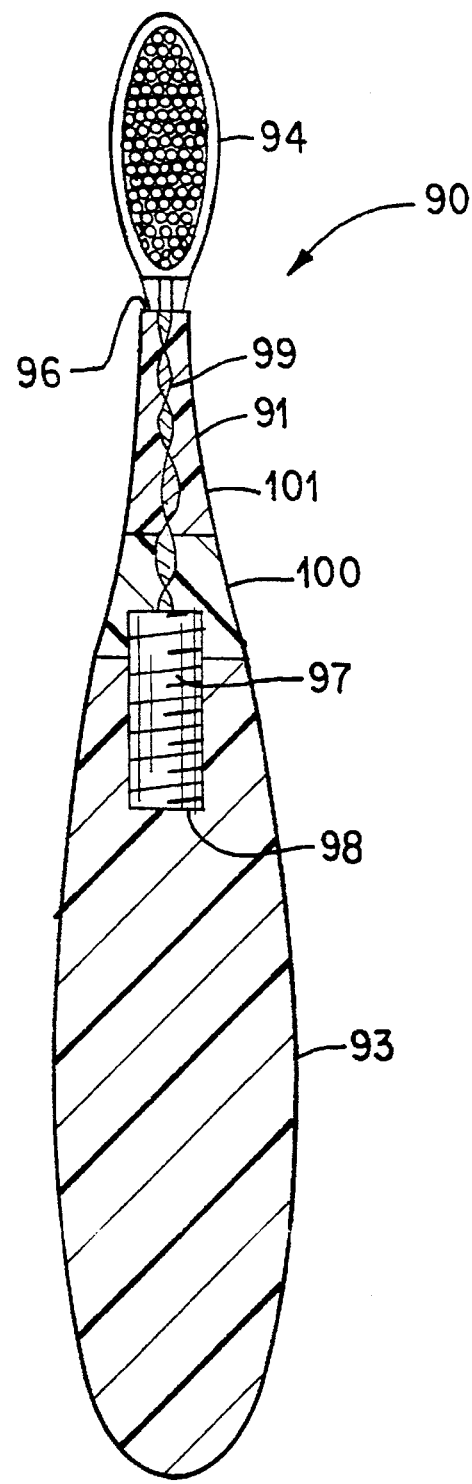
FIG. 14 is an orthographic view of said non-slanted toothbrush of said storage apparatus, taken along lines 14—14 of FIG. 13.
Figure 15:
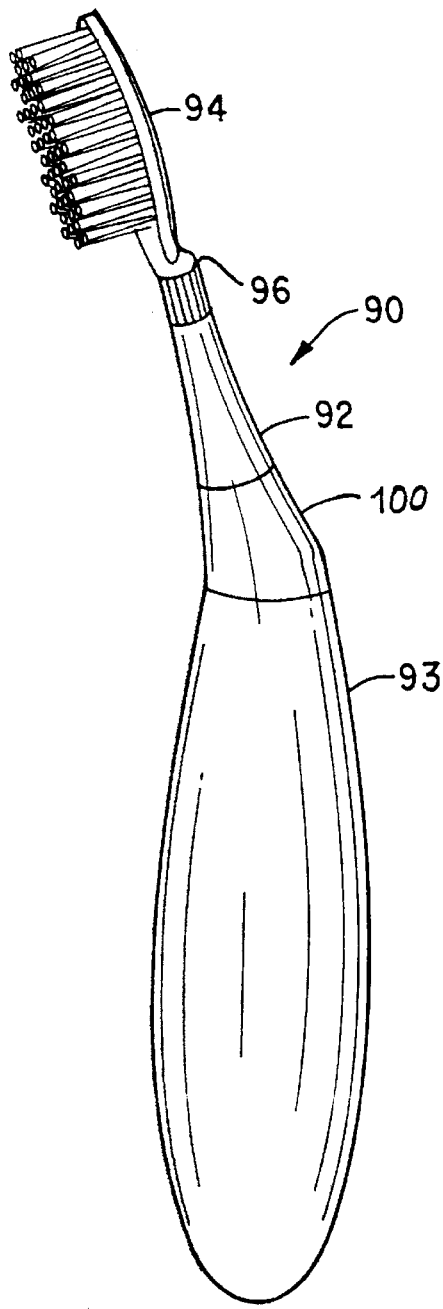
FIG. 15 is a perspective view of a slanted toothbrush of said storage apparatus

Referring to FIGS. 1–4, 6, and 13–15, the housing 2 is shown to store toothbrushes 90 that have a non-slanted shaft section 91 or a slanted shaft section 92, a handle 93 and bristle base 94, which is secured to the top end 96 of the non-slanted shaft section 91 or slanted shaft section 92. As shown in FIGS. 14 and 15, the non-slanted shaft section 91 and the slanted shaft section 92 each have a first screw attachment 97 extending from its base 100, which is operative to be rotatably inserted within a first threaded slot 98 located on the top section of their respective handle 93, thereby securing the non-slanted shaft section 91 and the slanted shaft section 92 to its respective handle 93. The non-slanted shaft section 91 and the slanted shaft section 92 each have a resilient wire core 99 located at the center of its respective shaft section, a shaft base 100 that is preferably made from a hard plastic material, and a shaft extension member 101 that is preferably made from a soft flexible plastic. The wire core 99 is designed to provide a gentle consistent force, minimizing soft tissue trauma or enamel wear. An alternate embodiment of the non-slanted shaft section 91 and the slanted shaft section 92 can consist of a solid plastic material without having a wire core 99.

Referring to FIGS. 13–15, the handle 93 can be made from a hard or flexible plastic material and has an anatomically designed grip. The bristle base 94 preferably is made of a plastic material and has a convex or slightly rounded shape. The bristle base 94 has a toothbrush bristles attached thereto that have an alternating long/short height design and are adapted to provide a uniform massaging of a user's teeth and gums in conjunction with a rotary motion of the toothbrushes 90. The rotary motion is desirable for optimal cleaning and gum stimulation. The bristle base 94 and its respective non-slanted shaft section 91 or slanted shaft section 92 are designed to be replaced after three months of use.

Figure 16:
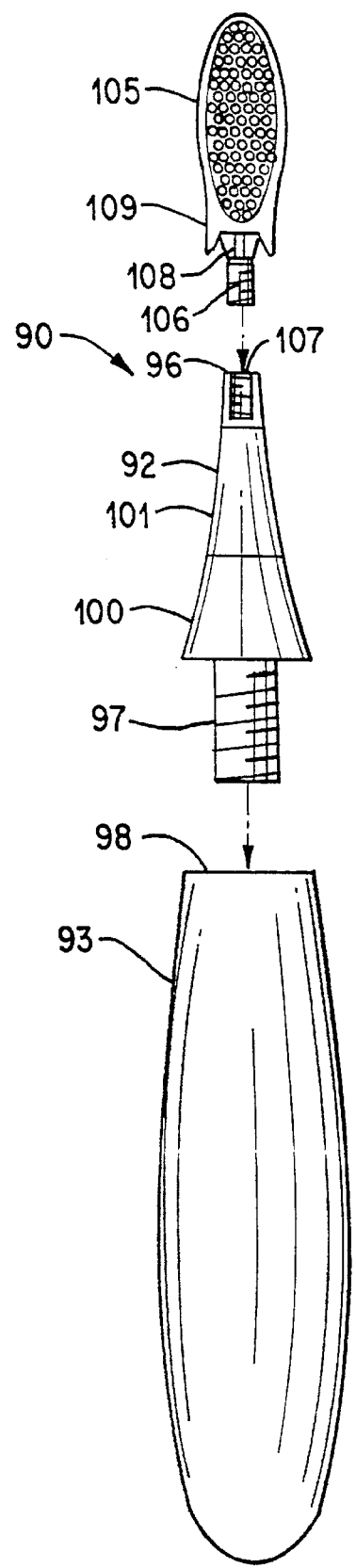
FIG. 16 is an exploded isometric view of an alternate embodiment of a toothbrush of said storage apparatus.

As shown in FIG. 16, an alternate embodiment of the toothbrushes 90 includes a removable and replaceable bristle base 105 that has a second screw attachment 106 located at the bottom of the bristle base 105. The second screw attachment 106 is adapted to be removably inserted and screwed into a second threaded slot 107 located at the top end 96 of the non-slanted shaft section 91 or the slanted shaft section 92. The bristle base 105 also has resilient memory wire strands 108, which can be made of nickel titanium material. The wire strands 108 extend from the second screw attachment 106 to a protective soft tissue shield 109. The soft tissue shield 109 has the toothbrush bristles attached thereto. The wire strands 108 can be separate strands of wire (as shown in FIG. 16), or can be a thick cylinder core (not shown). The bristle base 105 is designed to be replaced every three months, without requiring the replacement of the shaft sections 91 or 92. The non-slanted shaft section 91 and the slanted shaft section 92 can be interchanged to make the toothbrushes 90 have a non-slanted or slanted shaft section.

6. Alternate Embodiment

Figure 17:
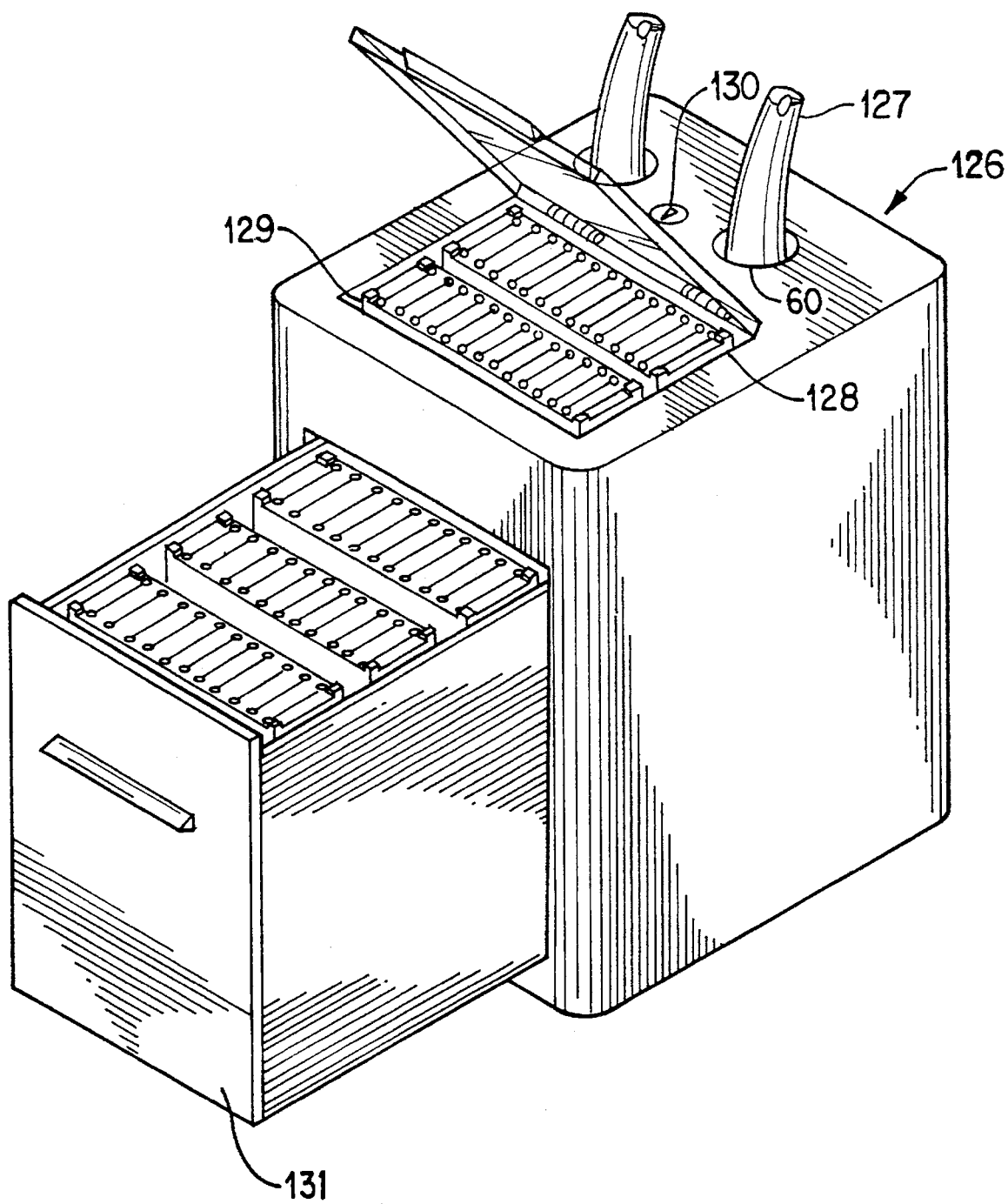
FIG. 17 is a perspective view of an alternate embodiment of the invention showing a dental floss tool stored within said storage apparatus and storage compartments for dental floss strand containers.
Figure 18:
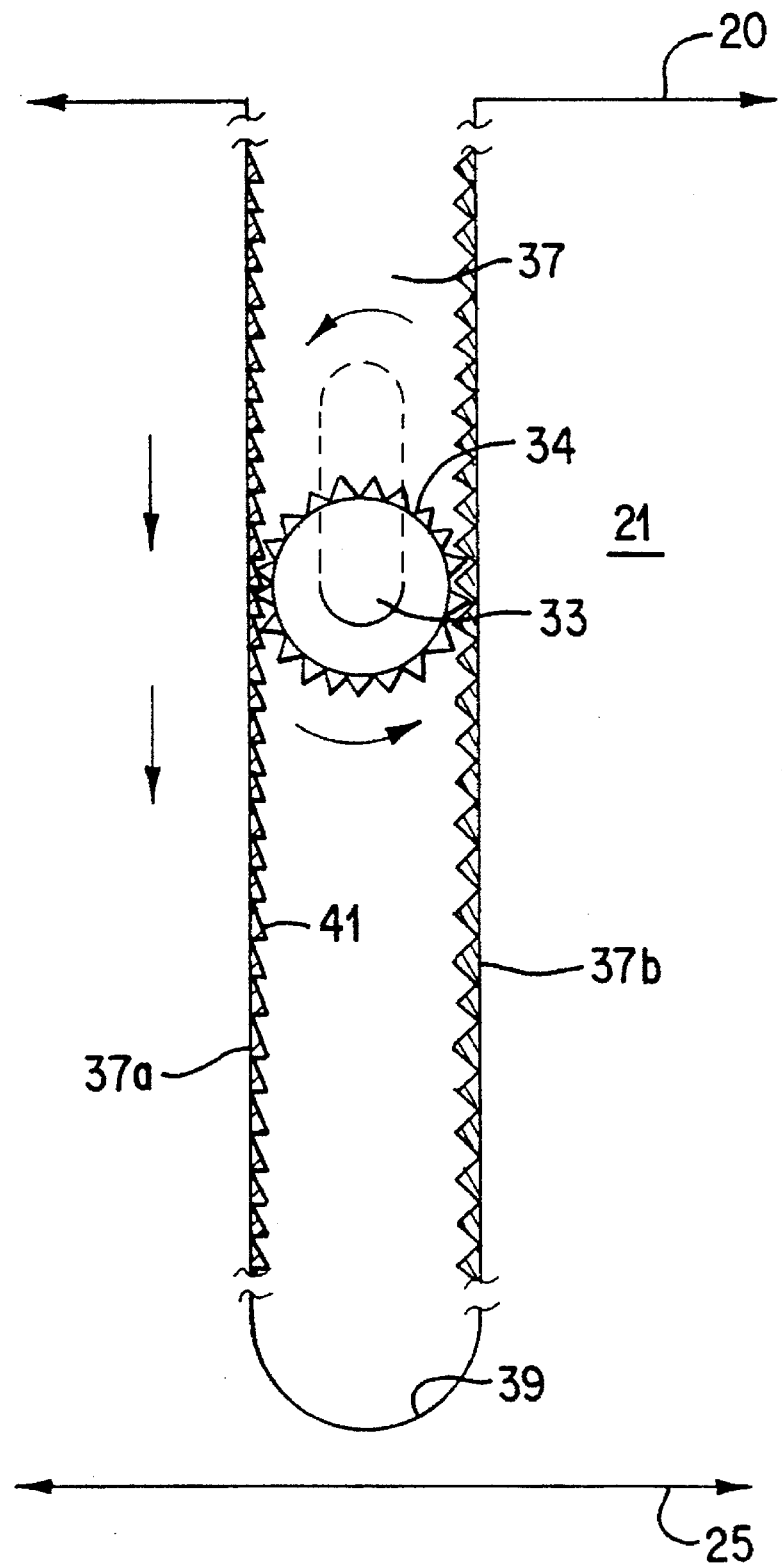
FIG. 18 is a side plan view of the toothpaste dispenser of said storage apparatus showing the gears the crank handle engaging the sides of the dispenser's slot.

Referring to FIG. 17, an alternative embodiment of the dental hygiene storage apparatus is shown by the reference numeral 126. The alternate hygiene storage apparatus 126 has a dental floss tool 127, a top storage area 128 that has storage capacity for dental floss containers 129, a floss strand cutter 130, and a front pull out drawer 131 for additional storage capacity. The alternate hygiene storage apparatus 126 does not have the toothpaste container 27 or the toothbrushes 90 which are included in the dental hygiene storage apparatus 1.

7. Summary

In operation, the dental hygiene storage apparatus 1 provides a user with the ability to use and store a dental floss tool 68, a toothpaste container 27 that has a toothpaste dispenser valve 30 with an auto-close clip 43, toothbrushes 90 that can have non-slanted or slanted top sections 91 and 92, respectively, a top storage section and a pull out drawer 121 for storing rectangular shaped containers 84, which have dental floss strands 70 stored therein. An alternate embodiment of the dental hygiene storage apparatus 126 is also shown to provide a user with the ability to store and use a dental floss tool 127, a top storage area 128 and a front pull out drawer 131 for storing dental floss containers 129, which have dental floss strands stored therein.

It is to be understood that while certain forms of this invention have been illustrated and described, the invention is not limited thereto, except insofar as such limitations are included in the following claims.

What is claimed and described to be secured by Letters Patent is as follows:

1. A dental hygiene storage apparatus having a dental floss device having first and second dental floss tools, each of said dental floss tools having separate, substantially elongated members with spaced apart top and bottom end portions, a gripping section located between said top and bottom end portions and an attachment means on each of said top end portion for releasably holding a dental floss segment without requiring a user to manipulate with said user's fingers said dental floss segment when attaching said dental floss segment to said attachment means, said members being of sufficient length to allow said user to insert said members into a person's mouth with said dental floss segment attached to said top end portion of said members to clean all surfaces of said person's teeth without requiring said user to insert said user's fingers into said person's mouth, said dental hygiene storage apparatus comprising:

(a) a housing having opposite spaced apart first and second side walls, opposite spaced apart front and rear walls, a top surface and a bottom surface, said opposite spaced apart first and second side walls and said opposite spaced apart front and rear walls each having spaced apart upper and lower ends, said upper ends joined to said top surface, said lower ends joined to said bottom surface;

(b) a storage compartment formed in said top surface and defined by spaced apart third and fourth side walls and spaced apart first and second end walls;

(c) a plurality of tubular cavities formed in said top surface and being spaced from said storage compartment, each of said tubular cavities being defined by tubular cavity walls extending from said top surface to a tubular cavity floor, said first and second dental floss tools removably stored within said tubular cavities; and (d) a pull out drawer removably inserted in said front wall, said drawer compartment being defined by spaced apart fifth and sixth side walls and spaced apart third and fourth end walls, said drawer having a handle attached to the front side of said pull-out drawer.

2. A dental hygiene storage apparatus as set forth in claim 1, wherein said top surface has a protruding prong having means for cutting said dental floss segments.

3. A dental hygiene storage apparatus as set forth in claim 1, wherein said dental hygiene storage apparatus has a removable partition extending from said front wall to a housing inner wall and forming a toothpaste compartment to dispense toothpaste therefrom, said toothpaste compartment having a partition front wall adjacent to and integral with a partition floor, said partition front wall having an aperture located adjacent to said partition floor, said toothpaste compartment further having a replaceable toothpaste container, a means for removably holding said toothpaste container in said toothpaste compartment and means for dispensing toothpaste from said toothpaste container through said aperture.

4. A dental hygiene storage apparatus having a dental floss device having first and second dental floss tools, each of said dental floss tools having separate, substantially elongated members with spaced apart top and bottom end portions, a gripping section located between said top and bottom end portions and an attachment means on each of said top end portions for releasably holding a dental floss segment without requiring a user to manipulate with said user's fingers said dental floss segment when attaching said dental floss segment to said attachment means, said members being of sufficient length to allow said user to insert said members into a person's mouth with said dental floss segment attached to said top end portion of said members to clean all surfaces of said person's teeth without requiring said user to insert said user's fingers into said person's mouth, said dental hygiene storage apparatus comprising:

(a) a housing having opposite spaced apart first and second side walls, opposite spaced apart front and rear walls, a top surface and a bottom surface, said opposite spaced apart first and second side walls and said opposite spaced apart front and rear walls each having spaced apart upper and lower ends, said upper ends joined to said top surface, said lower ends joined to said bottom surface;

(b) a storage compartment formed in said top surface and being defined by spaced apart third and fourth side walls and spaced apart first and second end walls extending from said top surface to a storage compartment floor;

(c) a plurality of tubular cavities spaced from said storage compartment, each of said tubular cavities being defined by tubular cavity walls extending from said top surface to a tubular cavity floor, said first and second dental floss tools removably stored within said tubular cavities;

(d) a door hingeably mounted adjacent to one of said storage compartment to gain access to said storage compartment; and (e) a pull out drawer removably inserted in a drawer compartment formed in said front wall, said drawer compartment being defined by spaced apart fifth and sixth side walls and spaced apart third and fourth end walls.

5. A dental hygiene storage apparatus as set forth in claim 4, wherein said dental hygiene storage apparatus has a removable partition extending from said front wall to a housing inner wall and forming a toothpaste compartment to dispense toothpaste therefrom, said toothpaste compartment having a partition front wall adjacent to and integral with a partition floor, said partition front wall having an aperture located adjacent to said partition floor, said toothpaste compartment further having a replaceable toothpaste container, a means for removably holding said toothpaste container in said toothpaste compartment and means for dispensing toothpaste from said toothpaste container through said aperture.

6. A dental hygiene storage apparatus having a dental floss device having first and second dental floss tools, each of said dental floss tools having separate, substantially elongated members with spaced apart top and bottom end portions, a gripping section located between said top and bottom end portions and an attachment means on each of said top end portions for releasably holding a dental floss segment without requiring a user to manipulate with said user's fingers said dental floss segment when attaching said dental floss segment to said attachment means, said members being of sufficient length to allow said user to insert said members into a person's mouth with said dental floss segment attached to said top end portion of said members to clean all surfaces of said person's teeth without requiring said user to insert said user's fingers into said person's mouth, said dental hygiene storage apparatus comprising:

(a) a housing having opposite spaced apart first and second side walls, opposite spaced apart front and rear walls, a top surface and a bottom surface, said opposite spaced apart first and second side walls and said opposite spaced apart front and rear walls each having spaced apart upper and lower ends, said upper ends joined to said top surface, said power ends joined to said bottom surface;

(b) a removable partition extending from said front wall to a housing inner wall and forming a toothpaste compartment to dispense toothpaste therefrom, said toothpaste compartment having a partition front wall adjacent to and integral with a partition floor, said partition front having an aperture located adjacent to said partition floor, said toothpaste compartment further having a replaceable toothpaste container, a means for removably holding said toothpaste container in said toothpaste compartment and means for dispensing toothpaste from said toothpaste container through said aperture;

(c) a storage compartment formed in said top surface and defined by spaced apart third and fourth side walls and spaced apart first and second end walls;

(d) a plurality of tubular cavities formed in said top surface and being spaced from said storage compartment, each of said tubular cavities being defined by tubular cavity walls extending from said top surface to a tubular cavity floor; and (e) a pull out drawer removably inserted in said front wall, said drawer compartment being defined by spaced apart fifth and sixth side walls and spaced apart third and fourth end walls, said drawer having a handle attached to the front side of said pull-out drawer.

7. A dental hygiene storage apparatus having a dental floss device having first and second dental floss tools, each of said dental floss tools having separate, substantially elongated members with spaced apart top and bottom end portions and a gripping section located between said top and bottom end portions, said dental hygiene storage apparatus comprising:

(a) a housing having opposite spaced apart first and second side walls, opposite spaced apart front and rear walls, a top surface and a bottom surface, said opposite spaced apart first and second side walls and said opposite spaced apart front and rear walls each having spaced apart upper and lower ends, said upper ends joined to said top surface, said lower ends joined to said bottom surface;

(b) a removable partition extending from said front wall to a housing inner wall and forming a toothpaste compartment to dispense toothpaste therefrom, said toothpaste compartment having a partition front wall adjacent to and integral with a partition floor, said partition front having an aperture located adjacent to said partition floor, said toothpaste compartment further having a replaceable toothpaste container, a means for removably holding said toothpaste container in said toothpaste compartment and means for dispensing toothpaste from said toothpaste container through said aperture;

(c) a storage compartment formed in said top surface and defined by spaced apart third and fourth side walls and spaced apart first and second end walls;

(d) a plurality of tubular cavities formed in said top surface and being spaced from said storage compartment, each of said tubular cavities being defined by tubular cavity walls extending from said top surface to a tubular cavity floor, said first and second dental floss tools removably stored within said tubular cavities;

(e) a door hingeably mounted adjacent to said spaced apart first end wall to gain access to said storage compartment; and (f) a pull out drawer removably inserted in said front wall, said drawer compartment being defined by spaced apart fifth and sixth side walls and spaced apart third and fourth end walls, said drawer having a handle attached to the front side of said pull-out drawer, said dental floss device further having an attachment means on each of said top end portions of said members for releasably holding one of said dental floss segments without requiring a user to manipulate with said user's fingers said dental floss segment when attaching said dental floss segment to said attachment means, said members being of sufficient length to allow said user to insert said members into a person's mouth with said dental floss segment attached to said top end portion of said members to clean all surfaces of said person's teeth without requiring said user to insert said user's fingers into said person's mouth, said user not having to manipulate said dental floss segment with said user's fingers when cleaning said person's teeth.

8. A dental hygiene storage apparatus having a dental floss device having first and second dental floss tools, each of said dental floss tools having separate, substantially elongated members with spaced apart top and bottom end portions, a gripping section located between said top and bottom end portions and an attachment means on each of said top end portions for releasably holding a dental floss segment without requiring a user to manipulate with said user's fingers said dental floss segment when attaching said dental floss segment to said attachment means, said dental hygiene storage apparatus comprising:

(a) a housing having opposite spaced apart first and second side walls, opposite spaced apart front and rear walls, a top surface and a bottom surface said opposite spaced apart first and second side walls and said opposite spaced apart front and rear walls each having apart upper and lower ends said upper ends joined to said to surface, said lower ends joined to said bottom surface;

(b) a removable partition extending from said front wall to a housing inner wall and forming a toothpaste compartment to dispense toothpaste therefrom, said partition having opposite spaced apart first and second partition side walls, opposite spaced apart front and rear walls, an open upper end and a partition floor, said partition side walls and said front and rear walls joined to said partition floor, said partition side walls each having a slot extending along partition side walls from said open upper end to proximate with said partition floor, said slots having gear protrusions said partition front wall having aperture located adjacent to said partition floor, said partition further having a compressor plate located within said partition, a gear removably inserted within each of said slots and adapted to travel along said gear protrusions, a shaft attached to said gears and having a shaft extension extending through one of said gears, said shaft positioned adjacent to and above said compressor plate, and a handle attached to said shaft extension and adapted for rotating said shaft and moving said gears along said slots, said compressor plate adapted to press against a removable toothpaste container located within said toothpaste compartment when said handle is rotated and said gears travel downward along said slots, said toothpaste container having a valve extending through said aperture for dispensing said toothpaste, said partition having a cover for enclosing said open upper end;

(c) a storage compartment formed in said top surface and defined by spaced apart third and fourth side walls and spaced apart first and second end walls;

(d) a plurality of tubular cavities formed in said top surface and being spaced from said storage compartment, each of said tubular cavities being defined by tubular cavity walls extending from said top surface to a tubular cavity floor, said first and second dental floss tools removably stored in said tubular cavities;

(e) a door hingeably mounted adjacent to said spaced apart first end wall to gain access to said storage compartment; and (f) a pull out drawer removably inserted in a drawer compartment formed in said front wail, said drawer compartment being defined by spaced apart fifth and sixth side walls and spaced apart third and fourth end walls, said drawer having a handle attached to the front side of said pull-out drawer.

* * * * *

UNITED STATES PATENT AND TRADEMARK OFFICE
CERTIFICATE OF CORRECTION

PATENT NO. : 5,662,130
DATED : September 2, 1997
INVENTOR(S) : Curtis B. Wiltshire It is certified that error appears in the above-identified patent and that said Letters Patent is hereby corrected as shown below:

On the title page:
In the section marked (56) please include the following prior art:

-- 2,643,795    Teal --

In Col. 11, Line 39:   "- said power ends joined to - " should be -- said lower ends joined to --.
In Col. 13, Line 6:    "- apart upper and lower ends - " should be -- apart upper and lower ends, --.
In Col. 13, Line 19:   "- gear protrusions -" should be -- gear protrusions, --.

Signed and Sealed this

Tenth Day of March, 1998

Attest:

BRUCE LEHMAN

Attesting Officer                Commissioner of Patents and Trademarks